(12) United States Patent
Griffith et al.

(10) Patent No.: US 7,807,150 B2
(45) Date of Patent: *Oct. 5, 2010

(54) INJECTABLE COMPOSITION CONTAINING CROSSLINKABLE MATERIAL AND CELLS FOR FORMING ANIMAL TISSUE

(75) Inventors: Linda G. Griffith, Cambridge, MA (US); Anthony Atala, Winston Salem, MA (US); Charles A. Vacanti, Uxbridge, MA (US); Keith T. Paige, Mercer Island, MA (US)

(73) Assignees: Massachusetts Institute of Technology, Cambridge, MA (US); Children's Medical Center Corporation, Boston, MA (US)

( * ) Notice: Subject to any disclaimer, the term of this patent is extended or adjusted under 35 U.S.C. 154(b) by 824 days.

This patent is subject to a terminal disclaimer.

(21) Appl. No.: 10/795,578

(22) Filed: Mar. 8, 2004

(65) Prior Publication Data

US 2004/0170612 A1 Sep. 2, 2004

Related U.S. Application Data

(63) Continuation of application No. 09/008,945, filed on Jan. 20, 1998, now Pat. No. 6,730,298, which is a continuation of application No. 08/056,140, filed on Apr. 30, 1993, now Pat. No. 5,709,854.

(51) Int. Cl.
*A61K 35/12* (2006.01)
*C12N 5/07* (2010.01)
*C12N 11/10* (2006.01)
*C12N 11/04* (2006.01)

(52) U.S. Cl. .............. 424/93.7; 424/426; 435/178; 435/182; 435/395; 435/396; 435/397

(58) Field of Classification Search .............. None
See application file for complete search history.

(56) References Cited

U.S. PATENT DOCUMENTS

| | | |
|---|---|---|
| 2,609,347 A | 9/1952 | Wilson |
| 2,653,917 A | 9/1953 | Hammon |
| 2,659,935 A | 11/1953 | Hammon |
| 2,664,366 A | 12/1953 | Wilson |
| 2,664,367 A | 12/1953 | Wilson |
| 2,846,407 A | 8/1958 | Wilson |
| 3,826,241 A | 7/1974 | Bucalo |
| 3,880,991 A | 4/1975 | Yolles |
| 3,883,393 A | 5/1975 | Knazek et al. |
| 3,902,497 A | 9/1975 | Casey |
| 3,949,073 A | 4/1976 | Daniels |
| 3,960,150 A | 6/1976 | Hussain et al. |
| 3,974,526 A | 8/1976 | Dardik et al. |
| 4,026,304 A | 5/1977 | Levy |
| 4,069,307 A | 1/1978 | Higuchi et al. |
| 4,137,921 A | 2/1979 | Okuzumi et al. |
| 4,141,087 A | 2/1979 | Shalaby et al. |
| 4,186,448 A | 2/1980 | Brekke |
| 4,192,827 A | 3/1980 | Mueller et al. |
| 4,205,399 A | 6/1980 | Shalaby et al. |
| 4,239,664 A | 12/1980 | Teng et al. |
| 4,243,775 A | 1/1981 | Rosensaft et al. |
| 4,277,582 A | 7/1981 | Mueller et al. |
| 4,280,954 A | 7/1981 | Yannas et al. |
| 4,304,591 A | 12/1981 | Mueller et al. |
| 4,304,866 A | 12/1981 | Green et al. |
| 4,347,847 A | 9/1982 | Usher |
| 4,348,329 A | 9/1982 | Chapman |
| 4,352,883 A | 10/1982 | Lim |
| 4,391,797 A | 7/1983 | Folkman et al. |
| 4,391,909 A | 7/1983 | Lim |
| 4,416,986 A | 11/1983 | Markus et al. |
| 4,431,428 A | 2/1984 | Schmer |
| 4,438,198 A | 3/1984 | Schmer |
| 4,439,152 A | 3/1984 | Small |
| 4,440,921 A | 4/1984 | Allcock et al. |
| 4,446,234 A | 5/1984 | Russo et al. |
| 4,450,150 A | 5/1984 | Sidman |
| 4,456,687 A | 6/1984 | Green |
| 4,485,096 A | 11/1984 | Bell |
| 4,495,174 A | 1/1985 | Allcock et al. |

(Continued)

FOREIGN PATENT DOCUMENTS

EP 0282746 9/1988

(Continued)

OTHER PUBLICATIONS

Atala et al., Journal of Urology, vol. 150, No. 2, pp. 745-747 (Aug. 1993), Annual Meeting of Section on Urology, American Academy of Pediatrics, Oct. 10-15, 1992.*

(Continued)

*Primary Examiner*—David M Naff
(74) *Attorney, Agent, or Firm*—Pabst Patent Group LLP

(57) ABSTRACT

Slowly polymerizing polysaccharide hydrogels have been demonstrated to be useful as a means of delivering large numbers of isolated cells via injection. The gels promote engraftment and provide three dimensional templates for new cell growth. The resulting tissue is similar in composition and histology to naturally occurring tissue. This method can be used for a variety of reconstructive procedures, including custom molding of cell implants to reconstruct three dimensional tissue defects, as well as implantation of tissues generally.

11 Claims, No Drawings

U.S. PATENT DOCUMENTS

| | | | |
|---|---|---|---|
| 4,505,266 A | 3/1985 | Yannas et al. | |
| 4,520,821 A | 6/1985 | Schmidt et al. | |
| 4,544,516 A | 10/1985 | Hughes et al. | |
| 4,545,082 A | 10/1985 | Hood | |
| 4,546,500 A | 10/1985 | Bell | |
| 4,563,490 A | 1/1986 | Stol et al. | |
| 4,576,608 A | 3/1986 | Homsy | |
| 4,609,551 A | 9/1986 | Caplan et al. | |
| 4,637,931 A | 1/1987 | Schmitz | |
| 4,642,120 A * | 2/1987 | Nevo et al. | 424/422 |
| 4,673,566 A | 6/1987 | Goosen et al. | |
| 4,675,189 A | 6/1987 | Kent et al. | |
| 4,681,763 A | 7/1987 | Nathanson et al. | |
| 4,689,293 A | 8/1987 | Goosen et al. | |
| 4,721,096 A | 1/1988 | Naughton et al. | |
| 4,757,128 A | 7/1988 | Domb et al. | |
| 4,803,168 A | 2/1989 | Jarvis, Jr. | |
| 4,806,355 A | 2/1989 | Goosen et al. | |
| 4,846,135 A | 7/1989 | Tiphaine | |
| 4,853,324 A | 8/1989 | Viles et al. | |
| 4,868,121 A | 9/1989 | Scharp et al. | |
| 4,880,622 A | 11/1989 | Allcock et al. | |
| 4,891,225 A | 2/1990 | Langer et al. | |
| 4,904,259 A | 2/1990 | Itay | |
| 4,946,938 A | 8/1990 | Magill et al. | |
| 4,963,489 A | 10/1990 | Naughton et al. | |
| 4,988,761 A | 1/1991 | Ikada et al. | |
| 5,032,508 A | 7/1991 | Naughton et al. | |
| 5,041,138 A * | 8/1991 | Vacanti et al. | 424/422 |
| 5,053,050 A | 10/1991 | Itay | |
| 5,266,326 A * | 11/1993 | Barry et al. | 424/423 |
| 5,292,514 A * | 3/1994 | Capecchi et al. | 424/422 |
| 5,294,446 A * | 3/1994 | Schlameus et al. | 424/489 |
| 5,354,736 A * | 10/1994 | Bhatnagar | 514/14 |
| 5,667,778 A * | 9/1997 | Atala | 424/93.7 |
| 5,709,854 A * | 1/1998 | Griffith-Cima et al. | 424/93.7 |
| 5,804,178 A * | 9/1998 | Vacanti et al. | 424/93.7 |
| 6,730,298 B2 * | 5/2004 | Griffith-Cima et al. | 424/93.7 |

FOREIGN PATENT DOCUMENTS

| | | | |
|---|---|---|---|
| EP | 0339607 | | 11/1989 |
| EP | 0361957 | | 4/1990 |
| WO | WO 87/06120 | | 10/1987 |
| WO | WO 89/00413 | | 1/1989 |
| WO | WO 91/01720 | | 2/1991 |
| WO | WO 92/19195 | * | 1/1992 |
| WO | WO 92/06702 | | 4/1992 |
| WO | WO 92/19195 | | 11/1992 |
| WO | WO 94/07999 | | 4/1994 |
| WO | WO 94/21299 | | 9/1994 |

OTHER PUBLICATIONS

Atala et al., Cartilage Cells as a Potential Treatment for Reflux, Abstract Presented at the Annual Meeting of the American Academy of Pediatrics, San Francisco, CA, Oct. 10-15, 1992.*

Vacanti et al., J. Ped. Surg. vol. 23, 1988 (pp. 3-9).*

Alberts, et al., Molecular Biology of the Cell, Garland Science, New York pp. 893 and 894 (1983).

Allcock, et al., "Amphiphilic polyphosphazenes as membrane materials: influence of side group on radiation cross-linking", *Biomaterials*, 9(6):500-508 (1988).

Allcock, et al., "An Ionically Cross-Linkable Polyphosphazene: Poly[bis(carboxylatophenoxy)phosphazene] and its Hydrogels and Membranes," Macromolecules, 22(1):75 (1989).

Allcock, et al., "Glyceryl Polyphosphazenes: Synthesis, Properties, and Hydrolysis", *Macromolecules*, 21(7):1980-1985 (1988).

Allcock, et al., "Hydrolysis Pathways for Aminophosphazenes", *Inorg. Chem.*, 21(1):515-521 (1982).

Allcock, et al., "Polyphosphazenes with Etheric Side Groups: Prospective Biomedical and Solid Electrolyte Polymers", *Macromolecules*, 19(1):1508 (1983).

Allcock, et al., "Synthesis of Poly(amino acid alkyl ester)phosphazenes", *Macromolecules*, 10:824-830 (1977).

Allcock, et al., "Synthesis of Sugar-Substituted Cyclic and Polymeric Phosphazenes and Their Oxidation, Reduction, and Acetylation Reactions", *Macromolecules*, 16(4):715 (1983).

Allcock, et al., "Phosphonitrilic Compounds. XV. High Molecular Weight Poly[bis(amino)phosphazenes] and Mixed-Substituent Poly(aminophosphazenes)", *Inorg. Chem.*, 11(11):2584-2590 (1972).

Anderson, et al., Caltech Biology, (1987).

Anderson, et al., "Gene Expression in Implanted Rat Hepatocytes Following Retroviral-Mediated Gene Transfer", *Somatic Cell and Molecular Genetics*, 15:215-227 (1989).

Atala, et al., "Endoscopic Treatment of Reflux with Autologous Bladder Muscle Cells", American Academy of Pediatrics meeting held in Dallas, Texas on Oct. 23, 1994, Abstract.

Atala, et al., "Cartilage cells as potential treatment for reflux", (Abstracta) Presented at the Annual Meeting of the American Academy of Pediatrics, San Francisco, CA, Oct. 10-15, 1992.

Atala, et al., "Injectable Alginate Seeded with Chondrocytes as a Potential Treatment for Vesicoureteral Reflux", *Journal of Urology*, 150(2, part 2):745-747 (1993).

Backlund, Erik-Olof, et al., "Toward a Transplantation Therapy in Parkinson's Disease," *Annals of the N.Y. Academy of Science*, 495:658-673 (1987).

Ben-Ze Ev, A., et al., "Cell-Cell and Cell-Matrix Interactions Differentially Regulate in the Expression of Hepatic and Cytoskeletal Genes in Primary Cultures of Rat Hepatocytes", *Proc. Natl. Acad. Sci, USA*, 85:2161-2165 (1988).

Berrino, et al., "Surgical Correction of Breast Deformities Following Long-Lasting Complications of Polyurethane-Covered Implants", *Ann. Plast. Surg.*, 24:481-8 (1990).

Biers, "Organogensis' Human Artery Equivalent May Revolutionize Vascular Grafts" Genetic Engineering News, (1987).

Bissell, et al., "Interactions of Rat Hepatocytes with Type IV Collagen, Fibronectin and Laminin Matrices, Distinct Matrix-Controlled Modes of Attachment and Spreading", *European Journal of Cell Biology*, 40:72-78 (1986).

Bissell, et al., "Support of Cultured Hepatocytes by a Laminin-Rich Gel, Evidence of a Functionally Significant Subendothelial Matrix in Normal Rat Liver", *J. Clin. Invest.*, 79:801-812 (1987).

Bissell, et al., "The Role of Extracellular Matrix in Normal Liver", *Scand. J. Gastroenterol Suppl*, 151:1-7 (1988).

Bjorklund, "Final Discussion", *Annals of the N.Y. Academy of Science*, 495:676-686 (1987).

Bohn. et al., "Adrenal Medulla Grafts Enhance Recovery of Striatal Dopaminergic Fibers", *Science*, 238(4817):913-6 (1987).

"Brain Graft Seeks to Relieve Huntington Disease Patient," The New York Times (1988).

Brown, "Fibrin-Collagen Nerve Repair Device", Inventors:Russ Griffiths, Larry Stensaas and Ken Horch, Letter dated May 10, 1988.

Craig, et al., "A Biologic Comparison of Polyglactin 910 and Polyglycolic Acid Synthetic Absorbable Sutures", *Surgery Gynecology & Obstetrics*, 141(1):1-10 (1975).

Culliton, "Gore Tex Organoids and Genetic Drugs", *Science*, 246:747-749 (1989).

Da Silva, et al., "An In Vivo Model to Quantify Motor and Sensory Peripheral Nerve Regeneration Using Bioresorbable Nerve Guide Tubes", *Brain Research*, 342:307-315 (1985).

Davis, et al., "Human Amnion Membrane Serves as a Substratum for Growing Axons In Vitro and In Vivo", *Science*, 236:1106-1109 (1987).

Del Cerro, et al., "Retinal Transplants into the Anterior Chamber of the Rat Eye", *Neuroscience*, 21(3):707-23 (1987).

Doillon, et al., "Collagen-Based Wound Dressings: Control of the Pore Structure and Morphology", *Journal of Biomedical Materials Research*, 20:1219-1228 (1986).

Doillon, et al., "Epidermal Cells Cultured on a Collagen-Based Material", G.W. Bailey, Editor, Proceedings of the 44th Annual Meeting of the Electron Microscopy Society of America, (1986).

Folkman, et al., "Angiogenic Factors", *Science*, 235:442-447 (1987).
Fontaine, et al., "Optimization Studies on Retroviral Mediated Gene Transfer into Rat Hepatocytes: Implications for Gene Therapy", The Society of University Surgeons, Resident's Program, Cincinnati, Ohio (1992).
Gash, "Neural Transplantation: Potential Therapy for Alzheimer's Disease", *J. Neural Transm.*, [Suppl.] 24:301-8 (1987).
Gash, et al., "Amitotic Neuroblastoma Cells Used for Neural Implants in Monkeys", *Science*, 233(4771):1420-2 (1986).
Grande, et al., "Healing of Experimentally Produced Lesions in Articular Cartilage Following Chondrocyte Transplantation", *The Anatomical Record*, 218:142-148 (1987).
Grande, et al., "The Repair of Experimentally Produced Defects in Rabbit Articular Cartilage by Autologous Chondrocyte Transplantation," *J Orthop Res.* 7:208-218 (1989).
Grolleman, et al., "Studies on a bioerodible drug carrier system based on polyphosphazene Part I. Synthesis", *J. Controlled Release*, 3:143-154 (1986).
Harris, et al., "Silicone Rubber Substrata: A New Wrinkle in the Study of Cell Locomotion", *Science* 208:177-179 (1980).
Henry, et al., "Nerve Regeneration Through Biodegradable Polyester Tubes", *Exp. Neurol.*, 90(3):652-76 (1985).
Ingber, et al., "Cells as Tensegrity Structures: Architectural Regulation of Histodifferentiation by Physical Forces Transduced Over Basement Membrane", Gene Expression During Normal and Malignant Differentiation, L.C. Andersson, et al., 13-32 (Academic Press, Orlando, FL. 1985).
Ingber, et al., "Control of Capillary Morphogenesis: A Molecular System of Mechanical Switches", *J. Cell Biol.*, 107:797a (1988).
Ingber, et al., "Endothelial Growth Factors and Extracellular Matrix Regulate DNA Synthesis Through Modulation of Cell and Nuclear Expansion", *In Vitro Cellular & Developmental Biology*, 23(5):387-394 (1987).
Ingber, et al., "Growth Control through Fibronectin-Dependent Modulation of Cell Shape", *J. Cell Biol.*, 105:219a (1987).
Ingber, et al., "How Does Extracellular Matrix Control Capillary Morphogenesis?", *Cell*, 58:803-805 (1989).
Ingber, et al., "Mechanochemical Switching Between Growth and Differentiation During Fibroblast Growth Factor-Stimulated Angiogenesis Vitro: Role of Extracellular Matrix", *J. Cell Biol.*, 109:317-330 (1989).
Jauregui, et al., "Attachment and Long Term Survival of Adult Rat Hepatocytes in Primary Monolayer Cultures: Comparison of Different Substrata and Tissue Culture Media Formulations", *In Vitro Cellular & Development Biology*, 22(1):13-22 (1986).
Jones, et al., Implantation of cultured regenerate muscle cells into adult rat muscle, Exp. Neutol., 66:602-610 (1979).
Kleinman, et al, "Use of Extracellular Matrix Components for Cell Culture", *Analytical Biochemistry*, 166:1-13 (1987).
Kolata, "Parkinson Procedure: Fervor Turns to Disillusion", The New York Times, (1988).
Kordower, et al., "An in Vivo and in Vitro Assessment of Differentiated Neuroblastoma Cells as a Source of Donor Tissue for Transplantation", *Annals of the New York Academy of Sciences*, 495:606-622 (1987).
Kordower, et al., "Neuroblastoma Cells in Neural Transplants: A Neuroanatomical and Behavioral Analysis", *Brain Research*, 417(1):85-98 (1987).
Kusano, et al., Acta Japoni Hepato, 63:345-351 (Asahikawa, Japan 1989).
Leong, et al., "Bioerodible Polyanhydrides as Drug-Carriers Matrices. I: Characterization, Degradation, and Release Characteristics", *Journal of Biomedical Materials Research*, 19:941-955 (1985).
Letourneau, "Possible Roles for Cell-to-Substratum Adhesion in Neuronal Morphogenesis", *Developmental Biology*, 44:77-91 (1975).
Lewin, "Cloud over Parkinson's Therapy", *Science*, 240:390-392, (1988).
Lewin, "Disappointing Brain Graft Results", *Science*, 1407 (1988).
Li, et al., "Influence of a Reconstituted Basement Membrane and Its Components on Casein Gene Expression and Secretion in Mouse Mammary Epithelial Cells", *Proc. Natl. Acad. Sci. USA*, 84:136-140 (1987).

Lim, et al., "Microencapsulation of living cells and tissues", *J Pharm Sci.*, 70(4) 351-354 1981.
Macklis, et al., "Cross-Linked Collagen Surface for Cell Culture that is Stable, Uniform, and Optically Superior to Conventional Surfaces", *In Vitro Cellular & Developmental Biology*, 21:(3) part I, 189-194 (1985).
Madison, et al. "Nontoxic Nerve Guide Tubes Support Neovascular Growth in Transected Rat Optic Nerve", *Exp. Neurol.*, 86(3):448-61 (1984).
Madison, et al., "Increased Rate of Peripheral Nerve Regeneration Using Bioresorbable Nerve Guides and a Laminin-Containing Gel", *Exp. Neurol.*, 88(3):767-72 (1985).
Madison, et al., "Peripheral Nerve Regeneration With Entubulation Repair: Comparison of Biodegradeable Nerve Guides Versus Polyethylene Tubes and the Effects of a Laminin-Containing Gel", *Exp. Neurol.*, 95(2):387-90 (1987).
Marciano, et al., "Structural and Functional Relationships of Grafted Vasopressin Neurons", *Brain Res.*, 370(2):338-42 (1986).
Mesnil, et al., "Cell Contact but Not Junctional Communication (Dye Coupling) with Biliary Epithelial Cells is Required for Hepatocytes to Maintain Differentiated Functions", *Exper. Cell Res.*, 173:524-533 (1987).
Michalopoulos, et al., "Primary Culture of Parenchymal Liver cells on Collagen Membranes", Exper. *Cell. Res.*, 94:70-78 (1975).
Millaruelo, "Role of Plasminogen Activator and Its Inhibitors in Axonal Outgrowth and Regeneration In Vivo", *Caltech Biology* (1987).
Mooney, et al., "Switching from Differentiation to Growth in Hepatocytes: Control by Extracellular Matrix", *J. Cell. Biology*, 111(5):149a(1990).
Mooney, et al., "Control of Hepatocyte Function Through Polymer-Substrate Modulation", Thesis Proposal—Department of Chemical Engineering, Massachusetts Institute of Technology (1989).
Movitz, "Accessory Spleens and Experimental Splenosis Principles of Growth", *The Chicago Medical School Quarterly*, 26(4):183-187 (1967).
Nastelin, "Pancreatic Islet Cell Transplantation: Optimization of Islet Cell Adhesion by Altering Polymer Surface Characteristics", Harvard-M.I.T. Division of Health Sciences and Technology (1990).
Naughton, et al., "Granulopoiesis and Colony Stimulating Factor Production in Regenerating Liver", *Exp. Hematol.*, 10(5):451-458 (1982).
Naughton, et al., "Long-Term Growth of Rat Bone Marrow Cells in a Three-Dimensional Matrix", The Anatomical Record, 18(1):97A (1987).
Naughton, et al., "Erythropoietin Production by Macrophages in the Regenerating Liver", *Journal of Surgical Oncology*, 30:184-197 (1985).
Notter, et al., "Neuronal Properties of Monkey Adrenal Medulla In Vitro", *Cell Tissue Res.*, 244(1):69-76 (1986).
Nyilas, et al. "Peripheral Nerve Repair with Bioresorbable Prosthesis", *Trans. Am. Soc. Artif. Intern. Organs*, 29:307-13 (1983).
Oellrich, et al., "Biliary Atresia", *Neonatal Network*, 25-30 (1987).
Oliwenstein, "The Power of Plastics", *Discover*, 18 (1989).
Omery, et al., "A Nursing Perspective of the Ethical Issues Surrounding Liver Transplantation", *Heart & Lung*, 17(6) (1988).
Paige, et al., "De Novo Cartilage Generation Utilizing Calcium Alginate-Chondrocyte Constructs", 1993 Plastic Surgery Research Council meeting held in Houston, Texas between Apr. 28, 1993, and May 1, 1993, Abstract.
Pasik, *Annals of the N.Y. Academy of Science*, 495:674-675 (1987).
Patterson, et al., "Adrenal Chromaffin Cell-Derived Cholinergic Neurons for Brain Transplants", *Caltech Biology* (1987).
Patterson, et al., Caltech Biology, 199-200 (1987).
Perlow, "Brain Grafting as a Treatment for Parkinson's Disease", *Neurosurgery*, 20(2):335-342 (1987).
Pimpl, et al., "Experimentelle Studie zur Frage der Transplantatkonditionierung and Transplantatgrofe Bei Heterotoper Autologer Milztransplantation", *Lagenbecks Archiv.*, 37215-36218 (1984).
Pimpl, et al., "Perfusion of Autologous Splenic Grafts in Correlation with Specific Immunological Functions: An Experimental Study in Pigs", *Eur. Surg. Res.*, 19:53-61 (1987).

Pitman, et al., "The Use of Adhesives in Chondrocyte Transplantation Surgery: In-Vivo Studies", *Bulletin of the Hospital for Joint Diseases Orthopaedic Institute*, 49(2): 213-220 (1989).
Ptasinska-Urbanska, et al., "Intrascleral Introduction of Isolated Allogeneic Chondrocytes Capable of Cartilage Reformation in Rabbits; Possible Procedure in Treatment of Detachment of the Retina", *Exp. Eye Res.*, 24(3):241-247 (1977).
Redmond, et al., "Fetal Neuronal Grafts in Monkeys Given Methyphenyltetrahydropyridine", *The Lancet*, 1125-1127 (1986).
Redmond, et al., "Transplants of Primate Neurons", *Lancet*, 2(8514):1046 (1986).
Reid, et al. "Long-Term Cultures of Normal Ray Hepatocytes on Liver Biomatrix", *Ann. NY Acad. Sci.* (1980).
Rhine, et al., "Polymers for Sustained Macromolecule Release: Procedures to Fabricate Reproducible Delivery Systems and Control Release Kinetics", Journal of Pharmaceutical Sciences, 69(3) (1980).
Rosen, et al., "Bioerodible Polyanhydrides for Controlled Drug Delivery", Butterworth & Co., (Publishers) Ltd. (1983).
Rosen, et al., "Bioerodible Polymers for Controlled Release Systems", *Controlled Release Systems: Fabrication Technology II* (5):83-110 (1983).
Sapoznikova, et al., "Morphological Changes in Splenic Autografts Following Splenectomy: Experimental and Clinical Findings", *Biological Abstracts*, 86:76896 (1987); *Arkhiv Patologii*, 49(12):31-37 (1987).
Sasaki, "Neovascularization in the Splenic Autograft Transplanted into Rat Omentum as Studied by Scanning Electron Microscopy of Vascular Casts", *Virchows Arch. [Pathol. Anat.]*, 409:325-334 (1986).
Sawada, et al., "Effects of Extracellular Matrix Components of the Growth and Differentiation of Cultured Rat Hepatocytes", *In Vitro Cellular & Development Biology*, 23(4):267-273 (1987).
Schmeck, "Doctors Try to Capitalize on the Liver's Ability to Regenerate Itself", The New York Times Medical Science (1989).
Seckel, et al., "Nerve Regeneration Through Synthetic Biodegradable Nerve Guides: Regulation by the Target Organ", *Plast Reconstr. Surg.*, 74(2):173-81 (1974).
Shine, et al., "Cultured Peripheral Nervous System Cells Support Peripheral Nerve Regeneration Through Tubes in the Absence of Distal Nerve Stump", *J. Neuroscience Res.*, 14(4):393-401 (1985).
Shozo, et al., "Urinary incontinence in children with primary vesicouretal reflux", *Japan. J. Urol.*, 81(7):1039-1044 (1990).
Siegel, et al., "Controlled Release of Polypeptides and Other Macromolecules", *Pharmaceutical Research*, 2-10 (1984).
Sirica, et al., "Fetal Phenotypic Expression by Adult Rat Hepatocytes on Collagen Gel/Nylon Meshes", *Proc. National Academy Science USA*, 76(1):283-287 (1979).
Sirica, et al., "Use of Primary Cultures of Adult Rat Hepatocytes on Collagen Gel-Nylon Mesh to Evaluate Carcinogen-Induced Unscheduled DNA Synthesis", *Cancer Research*, 40:3259-3267 (1980).
Sladek, et al., "Reversal of Parkinsonism by Fetal Nerve Cell Transplants in Primate Brain", *Annals of the New York Academy of Sciences*, 495:641-657 (1987).
Sladek, et al., "Survival and Growth of Fetal Catecholamine Neurons Transplanted into Primate Brain", *Brain Res. Bull.*, 17(6):809-18 (1986).
Sladek, et al., "Neural Transplantation: A Call for Patience Rather Than Patients", *Science*, 240:386-388 (1988).
Sladek, et al., "Transplantation of Fetal Dopamine Neurons in Primate Brain Reverses MPTP Induced Parkinsonism", *Progress in Brain Research*, 71:309-323 (1987).

Stemple, "A Factor that Induces Adrenergic Differentiation in Avian Neural Crest Cells",Caltech Biology, (1987).
Structure & Function in Man pub: WB Saunders Co. 1982.
Sudhakaran, et al., "Modulation of Protein Synthesis and Secretion by Substratum in Primary Cultures of Ray Hepatocytes" *Exper. Cell Res.*, 167:505-516 (1986).
Sullivan, "Spinal Injury Research Yields a Glimmer of Hope", The New York Times (1987).
Tavassoli, et al., "Studies on Regeneration of Heterotopic Splenic Autotransplants", *Blood*, 41(5):701-709 (1973).
Thompson, et al., "Implantable Bioreactors: Modern Concepts of Gene Therapy", Current Communications in Molecular Biology: Therapeutic Peptides and Proteins, D. Marshak, ed., 143-147 (1989).
Thompson., et al., "Heparin-Binding Growth Factor 1 Induces the Formation of Organoid Neovascular Structures in Vivo", *Proc. Natl. Acad. Sci. U.S.A.*, 86:7928-7932 (1989).
Tomomura, et al.,"The Control of DNA Synthesis in Primary Cultures of Hepatocytes From Adult and Young Rats: Interactions of Extracellular Matrix Components, Epidermal Growth Factor, and the Cell Cycle", *J. Cellular Physiology*, 130(1):221-227 (1987).
Unipoint Industries, Inc., "Polyvinyl Alcohol Foam for Surgical and Industrial Use" (May 1983).
UNOS Update, "National Cooperative Transplantation Study Completed", The National Organ Procurement Transplantation Network, 7(10) (1991).
Urbanska, et al., "Intrascleral introduction of isolated allogeneic chondrocytes capable of cartilage reformation in rabbits; possible procedure in treatment of detachment of the retina", *Exp. Eye Res.*, 24(3):241-247 (1977).
Vacanti, "Beyond Transplantation", *Arch. Surgery*, 123:545-549 (1988).
Vacanti, et al., "Selective cell transplantation using bioabsorbable artificial polymers as matrices", *Journal of Pediatric Surgery*, 23(1 pt):3-9 (1988).
Vacanti, et al., "Synthetic polymers seeded with chondrocytes provide a template for new cartilage formation", *Plastic and Reconstructive Surgery*, 88(5):753-759 (1991).
Vacanti, et al., "Tissue engineered growth of new cartilage in the shape of a human ear using synthetic polymers seeded with chondrocytes", *Mat. Res. Soc. Symp. Proc.*, 252:367-374 (1992).
Vacanti, et al., "Injectable condrocyte-alginate suspension as a potential treatment for incontinence", *J. Urol.*, 149(4)Suppl:291A (1993) (accepted on Apr. 20, 1993, by the Japan Information Center for Science and Technology).
Vargo, et al., "Infection as a Complication of Liver Transplant", Critical Care Nurse, 9(4):52-62, 1989.
Viig, et al., "UV-Induced DNA Excision Repair in Rat Fibroblasts During Immortalization and Terminal Differentiation In Vitro", *Exp. Cell Res.*, 167:517-530 (1986).
Yannas, "Wound Tissue Can Utilize a Polymeric Template to Synthesize a Functional Extension of Skin", *Science*, 215:174-176 (1982).
Yannas, et al., "Artificial Skin: A Fifth Route to Organ Repair and Replacement", *Iss. Polym. Biomaterial*, 106:221-230 (1986).
Yannas, I.V., et al., "Polymeric Template Facilitates Regeneration of Sciatic Nerve Across 15MM", *Polym. Material Sci. Eng.*, 53:216-218 (1985).
Yarom, et al., "Enhancement of human muscle growth in diffusion chambers by bone marrow cells", *Virchows Arch B cell Pathol. Mol. Pathol.*, 41(1-2):171-180 (1982).

* cited by examiner

INJECTABLE COMPOSITION CONTAINING CROSSLINKABLE MATERIAL AND CELLS FOR FORMING ANIMAL TISSUE This application is a continuation of U.S. patent application Ser. No. 09/008,945, filed Jan. 20, 1998, now U.S. Pat. No. 6,730,298, which is a continuation of U.S. patent application Ser. No. 08/056,140, filed Apr. 30, 1993 and issued as U.S. Pat. No. 5,709,854, all of the above being incorporated herein in their entirety by reference.

BACKGROUND OF THE INVENTION

The present invention is generally in the area of creating new tissues using polysaccharide hydrogel-cell compositions.

Craniofacial contour deformities, whether traumatic, congenital, or aesthetic, currently require invasive surgical techniques for correction. Furthermore, deformities requiring augmentation often necessitate the use of alloplastic prostheses which suffer from problems of infection and extrusion. A minimally invasive method of delivering additional autogenous cartilage or bone to the craniofacial skeleton would minimize surgical trauma and eliminate the need for alloplastic prostheses. If one could transplant via injection and cause to engraft large numbers of isolated cells, one could augment the craniofacial osteo-cartilaginous skeleton with autogenous tissue, but without extensive surgery.

Unfortunately, attempts to inject dissociated cells subcutaneously or to implant dissociated tissues within areas of the body such as the peritoneum have not been successful. Cells are relatively quickly removed, presumably by phagocytosis and cell death.

Cells can be implanted onto a polymeric matrix and implanted to form a cartilaginous structure, as described in U.S. Pat. No. 5,041,138 to Vacanti, et al., but this requires surgical implantation of the matrix and shaping of the matrix prior to implantation to form a desired anatomical structure.

Accordingly, it is an object of the present invention to provide a method and compositions for injection of cells to form cellular tissues and cartilaginous structures.

It is a further object of the invention to provide compositions to form cellular tissues and cartilaginous structures including non-cellular material which will degrade and be removed to leave tissue or cartilage that is histologically and chemically the same as naturally produced tissue or cartilage.

Summary of the Invention

Slowly polymerizing, biocompatible, biodegradable hydrogels have been demonstrated to be useful as a means of delivering large numbers of isolated cells into a patient to create an organ equivalent or tissue such as cartilage. The gels promote engraftment and provide three dimensional templates for new cell growth. The resulting tissue is similar in composition and histology to naturally occurring tissue. In one embodiment, cells are suspended in a hydrogel solution and injected directly into a site in a patient, where the hydrogel hardens into a matrix having cells dispersed therein. In a second embodiment, cells are suspended in a hydrogel solution which is poured or injected into a mold having a desired anatomical shape, then hardened to form a matrix having cells dispersed therein which can be be implanted into a patient. Ultimately, the hydrogel degrades, leaving only the resulting tissue.

This method can be used for a variety of reconstructive procedures, including custom molding of cell implants to reconstruct three dimensional tissue defects, as well as implantation of tissues generally.

DETAILED DESCRIPTION OF THE INVENTION

Techniques of tissue engineering employing biocompatible polymer scaffolds hold promise as a means of creating alternatives to prosthetic materials currently used in craniomaxillofacial surgery, as well as formation of organ equivalents to replaced diseased, defective, or injured tissues. However, polymers used to create these scaffolds, such as polylactic acid, polyorthoesters, and polyanhydrides, are difficult to mold and hydrophobic, resulting in poor cell attachment. Moreover, all manipulations of the polymers must be performed prior to implantation of the polymeric material.

Calcium alginate and certain other polymers can form ionic hydrogels which are malleable and can be used to encapsulate cells. In the preferred embodiment described herein, the hydrogel is produced by cross-linking the anionic salt of alginic acid, a carbohydrate polymer isolated from seaweed, with calcium cations, whose strength increases with either increasing concentrations of calcium ions or alginate. The alginate solution is mixed with the cells to be implanted to form an alginate suspension. Then, in one embodiment, the suspension is injected directly into a patient prior to hardening of the suspension. The suspension then hardens over a short period of time. In a second embodiment, the suspension is injected or poured into a mold, where it hardens to form a desired anatomical shape having cells dispersed therein.

Polymeric Materials.

The polymeric material which is mixed with cells for implantation into the body should form a hydrogel. A hydrogel is defined as a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazines, and polyacrylates, which are crosslinked ionically, or block copolymers such as Pluronics™ or Tetronics™, polyethylene oxide-polypropylene glycol block copolymers which are crosslinked by temperature or pH, respectively.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly (phosphazenes), poly(acrylic acids), poly(methacrylic acids), copolymers of acrylic acid and methacrylic acid, poly (vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix. Due to these mild conditions, alginate has been the most commonly used polymer for hybridoma cell encapsulation, as described, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

Polyphosphazenes are polymers with backbones consisting of nitrogen and phosphorous separated by alternating single and double bonds. Each phosphorous atom is covalently bonded to two side chains ("R"). The repeat unit in polyphosphazenes has the general structure (1):

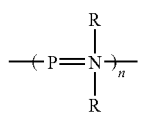

where n is an integer.

The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups. For example, a polyanionic poly[bis(carboxylatophenoxy)]phosphazene (PCPP) can be synthesized, which is cross-linked with dissolved multivalent cations in aqueous media at room temperature or below to form hydrogel matrices.

Bioerodible polyphosphazines have at least two differing types of side chains, acidic side groups capable of forming salt bridges with multivalent cations, and side groups that hydrolyze under in vivo conditions, e.g., imidazole groups, amino acid esters, glycerol and glucosyl. The term bioerodible or biodegradable, as used herein, means a polymer that dissolves or degrades within a period that is acceptable in the desired application (usually in vivo therapy), less than about five years and most preferably less than about one year, once exposed to a physiological solution of pH 6-8 having a temperature of between about 25° C. and 38° C. Hydrolysis of the side chain results in erosion of the polymer. Examples of hydrolyzing side chains are unsubstituted and substituted imidizoles and amino acid esters in which the group is bonded to the phosphorous atom through an amino linkage (polyphosphazene polymers in which both R groups are attached in this manner are known as polyaminophosphazenes). For polyimidazolephosphazenes, some of the "R" groups on the polyphosphazene backbone are imidazole rings, attached to phosphorous in the backbone through a ring nitrogen atom. Other "R" groups can be organic residues that do not participate in hydrolysis, such as methyl phenoxy groups or other groups shown in the scientific paper of Allcock, et al., *Macromolecule* 10:824-830 (1977).

Methods for synthesis and the analysis of various types of polyphosphazenes are described by Allcock, H. R.; et al., *Inorg. Chem.* 11, 2584 (1972); Allcock, et al., *Macromolecules* 16, 715 (1983); Allcock, et al., *Macromolecules* 19, 1508 (1986); Allcock, et al., *Biomaterials*, 19, 500 (1988); Allcock, et al., *Macromolecules* 21, 1980 (1988); Allcock, et al., *Inorg. Chem.* 21(2), 515-521 (1982); Allcock, et al., *Macromolecules* 22, 75 (1989); U.S. Pat. Nos. 4,440,921, 4,495, 174 and 4,880,622 to Allcock, et al.; U.S. Pat. No. 4,946,938 to Magill, et al.; and Grolleman, et al., *J. Controlled Release* 3, 143 (1986), the teachings of which are specifically incorporated herein by reference.

Methods for the synthesis of the other polymers described above are known to those skilled in the art. See, for example *Concise Encyclopedia of Polymer Science* and *Polymeric Amines and Ammonium Salts*, E. Goethals, editor (Pergamen Press, Elmsford, N.Y. 1980). Many polymers, such as poly (acrylic acid), are commercially available.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, and tin, although di-, tri- or tetra-functional organic cations such as alkylammonium salts, e.g., $R_3N^+$—\/\/\/—$^+NR_3$ can also be used. Aqueous solutions of the salts of these cations are added to the polymers to form soft, highly swollen hydrogels and membranes. The higher the concentration of cation, or the higher the valence, the greater the degree of cross-linking of the polymer. Concentrations from as low as 0.005 M have been demonstrated to cross-link the polymer. Higher concentrations are limited by the solubility of the salt.

The preferred anions for cross-linking of the polymers to form a hydrogel are divalent and trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.

Sources of Cells.

Cells can be obtained directed from a donor, from cell culture of cells from a donor, or from established cell culture lines. In the preferred embodiments, cells are obtained directly from a donor, washed and implanted directly in combination with the polymeric material. The cells are cultured using techniques known to those skilled in the art of tissue culture.

Cell attachment and viability can be assessed using scanning electron microscopy, histology, and quantitative assessment with radioisotopes. The function of the implanted cells can be determined using a combination of the above-techniques and functional assays. For example, in the case of hepatocytes, in vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with P-glucuronidase. Diconjugated and monoconjugated bilirubin can also be determined by thin layer chromatography after alkalinemethanolysis of conjugated bile pigments. In general, as the number of functioning transplanted hepatocytes increases, the levels of conjugated bilirubin will increase. Simple liver function tests can also be done on blood samples, such as albumin production. Analogous organ function studies can be conducted using techniques known to those skilled in the art, as required to determine the extent of cell function after implantation. For example, islet cells of the pancreas may be delivered in a similar fashion to that specifically used to implant hepatocytes, to achieve glucose regulation by appropriate secretion of insulin to cure diabetes. Other endocrine tissues can also be implanted. Studies using labelled glucose as well as studies using protein assays can be performed to quantitate cell mass on the polymer scaffolds. These studies of cell mass can then be correlated with cell functional studies to determine what the appropriate cell mass is. In the case of chondrocytes, function is defined as providing appropriate structural support for the surrounding attached tissues.

This technique can be used to provide multiple cell types, including genetically altered cells, within a three-dimensional scaffolding for the efficient transfer of large number of cells and the promotion of transplant engraftment for the purpose of creating a new tissue or tissue equivalent. It can also be used for immunoprotection of cell transplants while a new tissue or tissue equivalent is growing by excluding the host immune system.

Examples of cells which can be implanted as described herein include chondrocytes and other cells that form cartilage, osteoblasts and other cells that form bone, muscle cells, fibroblasts, and organ cells. As used herein, "organ cells" includes hepatocytes, islet cells, cells of intestinal origin, cells derived from the kidney, and other cells acting primarily to synthesize and secret, or to metabolize materials.

Addition of Biologically Active Materials to the Hydrogel.

The polymeric matrix can be combined with humoral factors to promote cell transplantation and engraftment. For example, the polymeric matrix can be combined with angiogenic factors, antibiotics, antiinflammatories, growth factors, compounds which induce differentiation, and other factors which are known to those skilled in the art of cell culture.

For example, humoral factors could be mixed in a slow-release form with the cell-alginate suspension prior to formation of implant or transplantation. Alternatively, the hydrogel could be modified to bind humoral factors or signal recognition sequences prior to combination with isolated cell suspension.

Methods of Implantation.

The techniques described herein can be used for delivery of many different cell types to achieve different tissue structures. In the preferred embodiment, the cells are mixed with the hydrogel solution and injected directly into a site where it is desired to implant the cells, prior to hardening of the hydrogel. However, the matrix may also be molded and implanted in one or more different areas of the body to suit a particular application. This application is particularly relevant where a specific structural design is desired or where the area into which the cells are to be implanted lacks specific structure or support to facilitate growth and proliferation of the cells.

The site, or sites, where cells are to be implanted is determined based on individual need, as is the requisite number of cells. For cells having organ function, for example, hepatocytes or islet cells, the mixture can be injected into the mesentery, subcutaneous tissue, retroperitoneum, properitoneal space, and intramuscular space. For formation of cartilage, the cells are injected into the site where cartilage formation is desired. One could also apply an external mold to shape the injected solution. Additionally, by controlling the rate of polymerization, it is possible to mold the cell-hydrogel injected implant like one would mold clay.

Alternatively, the mixture can be injected into a mold, the hydrogel allowed to harden, then the material implanted.

Specific Applications.

This technology can be used for a variety of purposes. For example, custom-molded cell implants can be used to reconstruct three dimensional tissue defects, e.g., molds of human ears could be created and a chondrocyte-hydrogel replica could be fashioned and implanted to reconstruct a missing ear. Cells can also be transplanted in the form of a thee-dimensional structure which could be delivered via injection.

The present invention will be further understood by reference to the following non-limiting examples.

EXAMPLE 1

Preparation of a Calcium-Alginate-chondrocyte Mixture and Injection into Mice to Form Cartilaginous Structures.

A calcium alginate mixture was obtained by combining calcium sulfate, a poorly soluble calcium salt, with a 1% sodium alginate dissolved in a 0.1 M potassium phosphate buffer solution (pH 7.4). The mixture remained in a liquid state at 4° C. for 30-45 min. Chondrocytes isolated from the articular surface of calf forelimbs were added to the mixture to generate a final cellular density of $1 \times 10^7$/ml (representing approximately 10% of the cellular density of human juvenile articular cartilage).

The calcium alginate-chondrocyte mixture was injected through a 22 gauge needle in 100 µl aliquots under the pannus cuniculus on the dorsum of nude mice.

The nude mice were examined 24 hours postoperatively, and all injection sites were firm to palpation without apparent diffusion of the mixture. Specimens were harvested after 12 weeks of in vivo incubation. On gross examination, the calcium alginate-chondrocyte specimens exhibited a pearly opalescence and were firm to palpation. The specimens weighed 0.11±0.01 gms (initial weight 0.10 gms). The specimens were easily dissected free of surrounding tissue and exhibited minimal inflammatory reaction. Histologically, the specimens were stained with hematoxylin and eosin and demonstrated lacunae within a basophilic ground glass substance.

Control specimens of calcium alginate without chondrocytes had a doughy consistency 12 weeks after injection and had no histologic evidence of cartilage formation.

This study demonstrates that an injectable calcium alginate matrix can provide a three dimensional scaffold for the successful transplantation and engraftment of chondrocytes.

Chondrocytes transplanted in this manner form a volume of cartilage after 12 weeks of in vivo incubation similar to that initially injected.

EXAMPLE 2

Effect of Cell Density on Cartilage Formation.

Varying numbers of chondrocytes isolated from the articular surface of calf forelimbs were mixed with a 1.5% sodium alginate solution to generate final cell densities of 0.0, 0.5, 1.0, and $5.0 \times 10^6$ chondrocytes/ml (approximately 0.0, 0.5, 1.0, and 5.0% of the cellular density of human juvenile articular cartilage). An aliquot of the chondrocyte-alginate solution was transferred to a circular mold 9 mm in diameter and allowed to polymerize at room temperature by the diffusion of a calcium chloride solution through a semi-permeable membrane at the base of the mold. The gels formed discs measuring 2 mm in height and 9 mm in diameter.

Discs of a fixed cellular density of $5 \times 10^6$ cells/ml were also formed in which the concentration of the sodium alginate and the molarity of the calcium chloride solutions were varied.

All discs were placed into dorsal subcutaneous pockets in nude mice. Samples were harvested at 8 and 12 weeks and examined for gross and histological evidence of cartilage formation.

Examinations of 8 and 12 week specimens revealed that a minimum cell density of $5 \times 10^6$ chondrocytes/ml was required for cartilage production which was observed only 12 weeks after implantation on gross examination, the specimens were discoid in shape and weighed 0.13±0.01 gms (initial weight 0.125 gms). The specimens were easily dissected free of surrounding tissue and exhibited minimal inflammatory reaction. Histologically, the specimens were stained with hematoxylin and eosin and demonstrated lacunae within a basophilic ground glass substance.

Cartilage formation was independent of calcium chloride concentration used in gel polymerization. Cartilage was observed in specimens with alginate concentrations varying from 0.5% to 4.0%; however, the lowest alginate concentration tested (0.5%) showed only microscopic evidence of cartilage.

Cartilage can be grown in a subcutaneous pocket to a pre-determined disc shape using calcium alginate gel as a support matrix in 12 weeks. Cartilage formation is not inhibited by either polymerization with high calcium concentrations or the presence of high alginate concentrations but does require a minimum cellular density of $5 \times 10^6$ cells/ml.

The ability to create a calcium alginate-chondrocyte gel in a given shape demonstrates that it is possible to use this technique to custom design and grow cartilaginous scaffolds for craniofacial reconstruction. Such scaffolds have the potential to replace many of the prosthetic devices currently in use.

EXAMPLE 3

Preparation of Implantable Premolded Cell-polymer Mixtures.

250 µl aliquots of an isolated chondrocyte suspension was mixed with 750 µls of a 2% (w/v) sodium alginate solution (0.1 M $K_2HPO_4$, 0.135 M NaCl, pH 7.4). A 125 µl aliquot was placed into 9 mm diameter cell culture inserts with 0.45 µm pore size semipermeable membranes. The cell-alginate mixture was placed into contact with a 30 mM $CaCl_2$ bath and allowed to polymerize for 90 minutes at 37° C. After 90 minutes, the cell-alginate gel constructs were removed from the mold and had a diameter of 9 mm and a height of 2 mm. The discs were placed into the wells of 24-well tissue culture plates and incubated at 37° C. in the presence of 5% $CO_2$ with 0.5 ml of a solution containing Hamm's F-12 culture media (Gibco, Grand Island, N.Y.) and 10% fetal calf serum (Gibco, Grand Island, N.Y.) with L-glutamine (292 µg/ml), penicillin (100 U/ml), streptomycin (100 µg/ml) and ascorbic acid (5 µg/ml) for 48 hrs.

Using this method, bovine chondrocyte-alginate discs were prepared, then implanted in dorsal subcutaneous pockets in athymic mice using standard sterile technique. After one, two, and three months, athymic mice were sacrificed, and the gel/chondrocyte constructs removed, weighed and placed in appropriate fixative. The cell-polymer complexes were studied by histochemical analysis.

Cartilage formation was observed histologically after three months of in vivo incubation at an initial chondrocyte density of $5 \times 10^6$ cell/ml.

The above protocol was modified by using a range of $CaCl_2$ concentration and a range of sodium alginate concentrations. Cartilage formation was observed using 15, 20, 30, and 100 mM $CaCl_2$ baths and 0.5, 1.0, 1.5, 2.0, and 4.0% sodium alginate solutions.

By changing the mold within which the cell-alginate construct is created, the shape of the implant can be customized. Additionally, the mold need not be semipermeable as calcium ion can be directly mixed with the cell-alginate solution prior to being placed within a mold. The key feature is that the construct can be fashioned into a given shape prior to implantation.

EXAMPLE 4

Preparation of Injectable Osteoblasts-hydrogel Mixtures.

Using the methodology described above, bovine osteoblasts have been substituted for chondrocytes and injected into animals using a hydrogel matrix.

Histology after 12 weeks of in vivo incubation showed the presence of early bone formation.

EXAMPLE 5

Use of the hydrogel matrix to form an immunoprotective matrix around the implanted cells.

By fashioning a cell-alginate construct as described above, one can use the hydrogel matrix to sterically isolate the encapsulated cells from the host immune system, and thereby allow allogenic cell transplants to form new tissues or organs without immunosuppression.

Bovine chondrocytes in an alginate suspension were transplanted into normal immune-competent mice. Histology after six weeks of in vivo incubation shows the presence of cartilage formation. Gross examination of the specimens does not demonstrate features of cartilage. Literature states that similar chondrocyte xenografts without alginate do not form cartilage.

Modifications and variations of the compositions and methods of the present invention will be obvious to those skilled in the art from the foregoing detailed description. Such modifications and variations are intended to come within the scope of the following claims.

We claim:

1. A composition for forming tissue in an animal comprising
   (a) an injectable solution of an ionically crosslinkable material forming a hydrogel when crosslinked,
   (b) an agent capable of ionically crosslinking the material, and
   (c) dissociated cells selected from the group consisting of cells that form cartilage, muscle cells, fibroblasts, and organ cells,
   wherein the cells are suspended in the crosslinkable material and the crosslinking agent is mixed with the cell suspension to form a hydrogel having cells suspended therein.

2. The composition of claim 1 wherein the material capable of forming a hydrogel is selected from the group consisting of alginate, polyphosphazincs, polyethylene oxide-polypropylene glycol block copolymers, poly(acrylic acids), poly(methacrylic acids), copolymers of acrylic acid and methacrylic acid, poly(vinyl acetate), and sulfonated polymers.

3. The composition of claim 2 wherein the ionically crosslinked material is further stabilized by cross-linking with a polyion.

4. The composition of claim 1 wherein the cells are organ cells.

5. The composition of claim 1 wherein the cells are chondrocytes.

6. The composition of claim 1 wherein between 1 and 5 million cells are suspended per ml of the composition.

7. The composition of claim 1 wherein between 0.5 and 5% of the cellular density of human juvenile articular cartilage cells are suspended per ml of the composition.

8. The composition of claim 1 wherein crosslinking of the hydrogel solution is initiated prior to implantation in the animal.

9. The composition of claim 1 wherein the hydrogel is injected into the animal as a cell suspension, which then crosslinks to form a hydrogel-cell suspension.

10. The composition of claim 2 wherein the crosslinking agent is calcium.

11. The composition of claim 1 wherein the agent capable of crosslinking the material comprises cations or anions, wherein the cations are selected from the group consisting of copper, calcium, aluminum, magnesium, strontium, barium, tin, and di-, tri- or tetra-functional organic cations; and the anions are selected from the group consisting of low molecular weight dicarboxylic acids, sulfate ions and carbonate ions.

* * * * *